(12) United States Patent
Abitbol et al.

(10) Patent No.: US 10,383,513 B2
(45) Date of Patent: Aug. 20, 2019

(54) OBJECTIVE PHOROPTER

(71) Applicant: VISIONIX LTD., Jerusalem (IL)

(72) Inventors: Marc Abitbol, Jerusalem (IL); Ran Yam, Jerusalem (IL); Haggai Herman, Givat Shmuel (IL); Ian Melnick, Jerusalem (IL); Aderet Sompolinsky, Jerusalem (IL)

(73) Assignee: VISIONIX LTD., Jerusalem (IL)

( * ) Notice: Subject to any disclaimer, the term of this patent is extended or adjusted under 35 U.S.C. 154(b) by 92 days.

(21) Appl. No.: 15/571,856

(22) PCT Filed: May 5, 2016

(86) PCT No.: PCT/IL2016/050482
§ 371 (c)(1),
(2) Date: Nov. 6, 2017

(87) PCT Pub. No.: WO2016/178237
PCT Pub. Date: Nov. 10, 2016

(65) Prior Publication Data
US 2018/0116505 A1 May 3, 2018

Related U.S. Application Data

(60) Provisional application No. 62/157,000, filed on May 5, 2015.

(51) Int. Cl.
A61B 3/10 (2006.01)
A61B 3/14 (2006.01)
(Continued)

(52) U.S. Cl.
CPC .......... A61B 3/1015 (2013.01); A61B 3/0285 (2013.01); A61B 3/117 (2013.01);
(Continued)

(58) Field of Classification Search
CPC ..... A61B 3/0285; A61B 3/1015; A61B 3/103; A61B 3/028; A61B 3/14; A61B 3/0008;
(Continued)

(56) References Cited

U.S. PATENT DOCUMENTS 6,736,509 B2  5/2004  Martino
7,357,509 B2  4/2008  Williams
(Continued)

FOREIGN PATENT DOCUMENTS

JP   H08-154896    6/1996
WO   2005/037090   4/2005
(Continued)

OTHER PUBLICATIONS

International Search Report and Written Opinion in PCT/IL2013/000037 published on Jul. 21, 2013.
(Continued)

*Primary Examiner* — Collin X Beatty
(74) *Attorney, Agent, or Firm* — AlphaPatent Associates, Ltd; Daniel J. Swirsky

(57) ABSTRACT

An objective phoropter utilizing an illuminated keratometric object projecting its illumination onto the subject's cornea, and imaging the reflection therefrom in an imaging camera. Image processing of these images is used to improve the focusing and centering of the cornea subject's eyes. Once the correctly focused position of the eyes is obtained relative to the keratometer object, an accurate longitudinal position of the eyes relative to the lens wheel assemblies can also be achieved. This results in more accurate prescription generation than in prior art systems where the eyes may not be accurately positioned relative to the lens wheels. Additionally, the lens combinations of the entire phoropter wheel can be calibrated using an artificial eye having adjustable levels of aberration. Each lens combination is adjusted to suppos-
(Continued)

edly correct a selected aberration level, and any residual aberration measured represents the correction to be applied to that lens combination.

17 Claims, 2 Drawing Sheets

(51) Int. Cl.
 *A61B 3/18* (2006.01)
 *A61B 3/028* (2006.01)
 *A61B 3/107* (2006.01)
 *A61B 3/117* (2006.01)
(52) U.S. Cl.
 CPC ................ *A61B 3/14* (2013.01); *A61B 3/145* (2013.01); *A61B 3/107* (2013.01); *A61B 3/18* (2013.01); *A61B 2560/0238* (2013.01)
(58) Field of Classification Search
 CPC ....... A61B 3/0091; A61B 3/145; A61B 3/117; A61B 3/107; A61B 2560/0238; A61B 3/18; A61F 2009/0088
 USPC ....... 351/206, 246, 205, 233, 239, 234, 216, 351/212, 235, 243
 See application file for complete search history.

(56) References Cited

U.S. PATENT DOCUMENTS

| | | | |
|---|---|---|---|
| 7,490,940 B2* | 2/2009 | Lai | A61B 3/1015 351/205 |
| 9,895,058 B2* | 2/2018 | Baker | A61B 3/103 |
| 2003/0081174 A1 | 5/2003 | Ross et al. | |
| 2004/0100619 A1 | 5/2004 | Olivier | |
| 2008/0018855 A1 | 1/2008 | Larichev | |
| 2009/0073384 A1 | 3/2009 | Warden | |
| 2010/0110379 A1 | 5/2010 | Zhou et al. | |
| 2011/0228225 A1 | 9/2011 | Liang | |

FOREIGN PATENT DOCUMENTS

| | | |
|---|---|---|
| WO | 2009/024981 | 2/2009 |
| WO | 2013/150513 | 10/2013 |

OTHER PUBLICATIONS

Extended European Search Report in EP application No. 13772990.1 published Dec. 22, 2015.
International Search Report and Written Opinion in PCT/IL2016/050482, dated Aug. 25, 2016.

* cited by examiner

OBJECTIVE PHOROPTER

FIELD OF THE INVENTION

The present invention relates to the field of objective phoropter measurements, using instruments incorporating iterative subjective phoropter measurements with objective wavefront analysis measurements, especially involving calibration methods for the lens wheels of the phoropter, and for increasing the accuracy of the centering and focusing, and of the longitudinal position of the eyes of the subject in the instrument during the measurements.

BACKGROUND OF THE INVENTION

There exist systems for performing combined phoropter and refractive measurements to ascertain the aberrations present in the eye of a subject. One such system is described in International Patent Publication No. WO/2013/150513, for "Objective Phoropter System" having common inventors with the present application, and co-assigned with the present application. That system uses a pair of phoropter wheel assemblies, one for each eye, each assembly comprising a number of lens wheels incorporating the series of lenses and wedges required to compensate for a wide range of refractive aberrations in the vision of the eye being tested. The vision of each eye is corrected by a combination of a subjective phoropter measurement, iteratively performed with an objective wavefront analysis measurement to determine the residual aberrations existing after the initial phoropter correction. The wavefront analysis measurement can be performed by any of the known methods, and particularly by the use of a Shack-Hartmann array to analyze the deviation of the retinal reflected wavefront from a planar wave, as is known in the art.

However, there are a number of shortcomings with such prior art systems. In the first place, the accuracy of the systems rely on the nominal values of the lenses used in the lens wheels, such that if any of the lenses have an inaccurate value, the supposed optical power of the lens combination used will be incorrect, and the prescription output for preparing correction spectacle lenses will be inaccurate. Such inaccuracy can also arise because of poor alignment of the lens wheels. As a result, the vision correction prescription will not provide the optimum correction possible for the subject.

Additionally, the subject's eyes may not be positioned at the correct distance from the phoropter lens wheels, and since this distance is important for prescribing lenses which will provide optimum correction in a spectacle frame which is designed to sit at a standard distance from the user's eyes, any deviation therefrom will result in less than optimum vision correction. Therefore, a more accurate method of ensuring the correct focal position of the eye relative to the phoropter lens wheels also needs to be provided. The same consideration applies to the lateral centering of the subject's eyes during the measurements, and prior art methods using the pupil image to center the eye during the measurements may not be optimal.

There therefore exists a need for an objective phoropter instrument which overcomes at least some of the disadvantages of prior art systems and methods.

The disclosures of each of the publications mentioned in this section and in other sections of the specification, are hereby incorporated by reference, each in its entirety.

SUMMARY

The present disclosure describes new exemplary systems for performing objective phoropter measurements. The objective phoropters described in this disclosure incorporate a number of novel methods and assemblies for improving the accuracy and convenience of use of the instruments. A first method uses a keratometric measurement system in order to focus and center the subject's eyes for the measurement. The system uses an illuminated keratometric object projecting its illumination onto the subject's cornea, and using the reflection therefrom, and an imaging camera to image that reflected light and to perform image processing thereon to improve the focussing and the centering of the subject's eyes. Once the correctly focused position of the eyes is obtained relative to the keratometer object, an accurate longitudinal position of the eyes relative to the lens wheel assemblies can also be achieved. This results in more accurate prescription generation than in prior art systems where the eyes may not be accurately positioned relative to the lens wheels.

In such prior art methods, the ophthalmist attempts to locate the longitudinal position of the eye by manual sighting. In the most commonly used method, a mirror is fixed at a predetermined position relative to the phoropter wheel assembly, and at an angle of 45° to a plane parallel to the corneal apex. The mirror has markings on it. The central mark corresponds to the best vertex distance (as will be further explained hereinbelow) from the lens wheels of the phoropter assembly and there are other marks at fixed distances from the central mark. The user views the mirror from a plane perpendicular to the axis of the eye and will see the front of the cornea on one of the marks, he can then move the head back and forth until the cornea is on the appropriate mark, thus defining the distance of the corneal apex from the lenses of the phoropter wheel assembly. According to another prior art method, a laser beam is projected across the front surface of the eyes, and the head moved forwards and backwards until the ophthalmist determines that a glancing position of the beam on the cornea has been obtained.

Another significant improvement described in this disclosure relates to a novel method of calibrating the lens wheel combinations used in order to correct the subject's vision during the phoropter measurement. In this method, the wavefront analysis module of the objective phoropter is used to measure the residual aberration of an artificial eye having a known visual aberration, after that aberration has been supposedly corrected with a phoropter lens combination selected to exactly compensate for the artificial eye's aberration. Any such residual aberration is due to the fact that the supposed optical power of the lens wheel assembly used to perform the correction is not exact, and the actual optical power should be adjusted by the level of residual aberration measured by the wavefront analysis system. The artificial eye, whose level of aberration can be determined very exactly, can be set to different aberration levels, and each lens wheel combination used to supposedly correct that aberration can have its true value calculated accordingly. By this means, the entire phoropter wheel, covering the entire measurement range can be accurately calibrated, resulting in more accurately prescribed correction lenses for the subject.

Other implementations enable the gaze angle of the subject to be corrected either by using the eye focussing measurement data, or by viewing the symmetry of the image of the keratometric reflection on the instrument display. Any lateral tilt of the head can also be determined and corrected.

There is thus provided in accordance with an exemplary implementation of the devices described in this disclosure, an improved accuracy objective phoropter, comprising:

(i) a combination objective phoropter instrument comprising a wavefront analysis system and a phoropter system incorporating a lens wheel array,
(ii) at least one illuminated object disposed in the field of view of an eye to be measured, and at a predefined distance from the phoropter wheel,
(iii) a camera system positioned such that it captures images of the reflection from the cornea of the eye, of the illumination of the at least one object, and
(iv) a control unit using the images from the camera to generate control instructions to perform at least one of (a) centering an axis of the instrument relative to the center of the eye, and (b) focusing the position of a lens wheel of the instrument relative to the cornea of the eye.

Such a phoropter may further incorporate lateral adjustment mechanisms for the lens wheel array, wherein the control instructions are input to the lateral adjustment mechanisms such that the lens wheel array moves in order to center its axis relative to the center of the eye. In such phoropters, the center of the eye may be determined as the position of the apex of the cornea of the eye.

Furthermore, according to additional implementations, the control unit may perform the focusing of the position of the lens wheel of the instrument relative to the cornea of the eye, by actuating longitudinal motion mechanisms of the instrument relative to the eye and determines when the images of the reflection from the cornea of the eye of the illumination of the at least one object, have maximum sharpness.

In any of the above described phoropters, the at least one illuminated object may be at least part of an illuminated ring. Additionally, the illumination should be at a wavelength other than that used for performing the wavefront analysis In yet other implementations, the control unit of the phoropter is further adapted to determine lack of symmetry of the images of the reflections from the cornea of both of the eyes, the lack of symmetry indicating that the gaze of at least one of the eyes is off-axis. In such a case, the control unit is configured to output control instructions to realign the subject's gaze in order to symmetrize the images of the at least one object.

Additionally, in any of the previously described phoropters, the control unit may further be adapted to determine lack of simultaneous correct focusing of the images of the reflection of the at least one object from the corneas of both of the eyes, the lack of simultaneous focusing indicating that the head of the subject whose eyes are being measured is not directed straight in the direction of the axis of the objective phoropter. In that situation, the control unit may further be adapted to output control instructions to realign the subject's head in order to bring the position of both of the eyes to focus simultaneously. These control instructions may comprise instructions for rotation of the subject's head, to bring the head on-axis.

In yet other implementations of the phoropters described hereinabove, the phoropter further comprises a test chart disposed at a distance in front of the eye representative of a near vision test, such that the objective phoropter instrument can determine the near vision correction required by the eye under test. This test chart should be axially adjustable to different near vision positions.

There is further provided in accordance with an exemplary method described in this disclosure, a method of calibrating the phoropter wheel assembly of an objective phoropter incorporating a wavefront analyser, comprising:

(i) positioning in front of a channel of the objective phoropter, an artificial eye having adjustable levels of vision aberration,
(ii) selecting a first level of vision aberration of the artificial eye,
(iii) selecting a first lens combination from the phoropter wheel assembly having a nominal optical power expected to provide correction to the first selected level of vision aberration of the artificial eye,
(iv) using the wavefront analyser to measure the residual level of vision aberration of the artificial eye corrected using the first lens combination,
(v) using the residual level of vision aberration to determine the true optical power of the first lens combination, and
(vi) repeating the procedure for further selected levels of vision aberration of the artificial eye and corresponding lens combinations from the phoropter wheel assembly.

In this method, the artificial eye may comprise a lens disposed in front of a diffusive reflector. Using such methods, the true optical powers of the lens combinations in the phoropter wheel assembly may be stored in a memory of the objective phoropter. The true optical power of the first lens combination may be determined by subtracting the measured residual level of vision aberration of the artificial eye from the nominal optical power of the first lens combination corrected using the first lens combination.

BRIEF DESCRIPTION OF THE DRAWINGS

The present invention will be understood and appreciated more fully from the following detailed description, taken in conjunction with the drawings in which.

DETAILED DESCRIPTION

Figure 1:
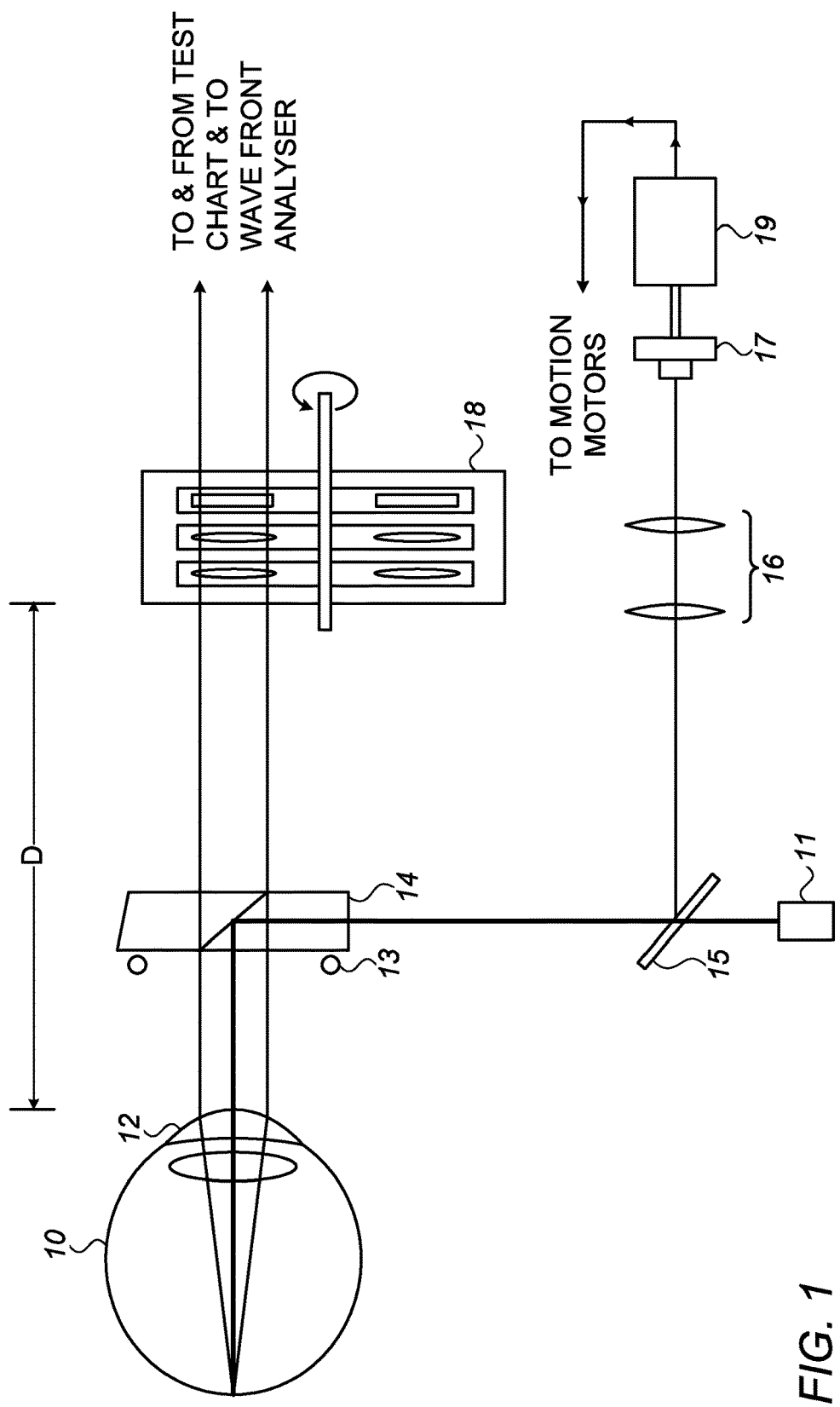
FIG. 1 shows schematically one exemplary implementation of an improved objective phoropter, including better focussing and centering configurations for the subject's eyes.

Accurate lateral centering and longitudinal focussing of the eye are important operations necessary for ensuring good accuracy for many ophthalmic measurements. The correct position of focus is important, not only for the phoropter measurement but also for the wavefront measurement of the present instrument. A pair of spectacles should be worn at a predetermined distant from the eye, in order that the prescription accurately compensates for the eye's aberrations. The correct distance is important because the image is effectively focused onto the subject's retina by a combination of the lens of the subject's eye and the spectacle lens in front of that eye. The longitudinal distance between those two lenses is one of the parameters that determines the power of such a combination of spaced lenses. It is for this reason that a standard distance D of the spectacle lenses from the front surface of the eye is assumed in ophthalmic prescriptions, and this convention is used for determining the manufactured dimensions of spectacle frames to ensure the correct distance of the lenses from the eye. For example, in the USA, this distance is generally standardized at 13.5 mm, while in Europe, a standard distance of 12 mm is used, but that can be modified over a range of 8 mm-18 mm for special situations, dependent on the required spectacle power and the shape of the subject's face. It is because of this dependence of the correction lens spacing from the eye, that it is important that the eye of the subject be correctly focused relative to the position of the lens wheels of the phoropter assembly. This is also important for the wavefront measurement. This effect of the lens-to-eye spacing on the power of the lens combination becomes more important the higher the power of the correction lenses used.

As explained above, one prior art method of ensuring the correct distance of the eye from the phoropter lens position is by using a beam projected laterally across the eyes of the subject, and then attempting to ascertain when the beam just skims the front surface of the cornea. A beam bending mirror having calibrated longitudinal positions, can be used to adjust the position of the lateral plane at which the beam crosses in front of the eye to be at the standard lens-to-eye distance D required, generally between 12 and 14 mm. The forehead rest is then adjusted until that lateral beam just grazes the front surface of the eye, and the correct eye-to-lens distance is then ensured. A more common prior art method is performed by just observing the position of the front of the eye through a mirror, without the use of a projected beam. However, both of these procedures depend on the skill of the operator performing the measurement, and a more accurate and an automatic method of longitudinally positioning the eye under test is desirable.

In some prior art objective phoropter instruments, such as that described in the above mentioned International publication WO/2013/150513, centering is performed using a source situated to the side of the subject's eye, so that it provides dark field illumination to the eye. The image of the pupil is then analyzed in the wavefront analysis section, and the Shack Hartman deflected spot image centered to provide centering of the subject's pupil. This method has the advantage that no additional camera channel is required for analyzing the image of the eye, but it has the disadvantage that it provides the center of the pupil of the subject, and there may be situations in which it is important to center the eye relative to the apex of the cornea, which may not be coincident with the center of the pupil. In the present described instrument, in order to accomplish accurate lateral centering and longitudinal focussing of the eye for the phoropter measurement, a keratometer measurement mode is provided. The keratometer measurement can be based on a simple illuminated object, such as a single ring, or even parts of a ring. An additional optical path besides that of the subjective phoropter measurement and that of the objective wavefront analysis measurement is used in order to perform the keratometric focusing and centering measurements.

Reference is made to FIG. 1 which shows one exemplary implementation of this arrangement. FIG. 1 shows the additions made to the prior art objective phoropter described in WO/2013/150513. The components common to that instrument include the phoropter wheel 18 containing the correction lenses, the laser 11 for performing the objective wavefront analysis, and the beam splitter 14 for introducing the laser beam into the optical path of the subjective phoropter channel. The subject's eye 10 and its cornea 12 are also shown.

In order to perform the centering and focusing procedure, an illumination source such as a single illuminated ring 13 is positioned in the field of view of the eye 10, in the region of the plane of the beamsplitter 14, and illuminates the cornea 12. The source 13, though shown in the example of FIG. 1 in front of the beamsplitter 14, could be positioned laterally outside of the beamsplitter, or even behind it. Although a complete ring is shown in this implementation, any other convenient illumination form such as one or more parts of a ring may likewise be used. The exact longitudinal position of the keratometric illuminated source 13 is important, since this defines a reference plane relative to which the eye's longitudinal position and that of the phoropter lenses is determined, and, as will be discussed below, the distance D of the eye from the phoropter wheel assembly is important to simulate the standard location of the ultimately prescribed spectacle lenses from the eye. Therefore, the position of this keratometric measurement illuminated source in the instrument will also determine the distance D of the eye from the phoropter wheel, since the position of the eye is determined relative to the instrument by the instrument's chin and forehead rest.

The keratometer ring should emit at a different wavelength $\lambda 1$ from that of both the phoropter measurement at $\lambda 2$, which is usually broadband visible room illumination, and the Shack Hartmann measurements at $\lambda 3$, so that the image of the keratometer ring reflected from the cornea can be separated by means of a wavelength selective component. Generally, the wavelengths of the keratometer illumination $\lambda 1$ and the wavefront analysis illumination $\lambda 3$ are in the infra-red or near infra-red, in order to avoid interfering with the subject's vision for the phoropter measurement, which is generally performed using white light in the visible. Often, 780 nm is used for the wavefront measurement at $\lambda 3$, and 880 nm for the keratometer measurement at $\lambda 1$, since these are readily available NIR sources, though any other suitable wavelengths may be used. The reflection from the cornea is directed by the phoropter beam splitter 14 to an additional beam splitter 15 where the keratometer image reflected from the cornea may be separated from the laser illumination $\lambda 3$, and is directed through a focusing lens pair 16 to a camera 17, having a two dimensional sensor array. When setting up the instrument, an artificial eye should be positioned at the correct corneal position relative to the lenses of the phoropter assembly, and the lens pair is moved backwards and forwards until a good focus is achieved on the camera. The lenses 16 are then fixed in place. Then, during any subsequent measurement, the whole phoropter is moved relative to the eye, until a good focus is achieved, and that focus is thus known to be the correctly focused position of the eye relative to the lens wheels of the phoropter assembly.

The camera outputs its images of the reflections of the illuminated keratometer ring to a control unit 19, where the images are analyzed. The control system uses image processing of the camera images for determining when the ring is at maximum sharpness, which defines the optimal focus distance. One such method is described in PCT International Publication Number WO2009/024981, where the maximum differences in the spatial derivatives of the ring illumination is used to define the position of maximum ring sharpness and hence of optimum focus, though any other suitable method may be used. The control system also actuates the motion motors for moving the measurement system towards or away from the eye in order to provide optimum focus of the images of the keratometer ring reflected from the cornea. When this optimum focus has been obtained, the keratometer illumination is correctly focused on the eye, and since the position of the keratometer ring is known, the correctly focused position of the eye to the rest of the instrument components is also known. In addition the control unit 19 may use image processing in order to determine the lateral position of the images of the keratometer ring reflected from the cornea, and to output control signals to the horizontal and vertical travel motors of the system to center those images, thus ensuring that the phoropter measurement is performed with the eye properly centered.

Although the keratometric measurement system is used and is so programmed in the presently described instrument, in order to accurately and automatically ensure correct centering and focusing of the subject's eyes relative to the axes and longitudinal positions of the lens wheels of the phoropter assembly, it is to be understood that the keratometric measurement system can also be used in order to perform a measurement of the corneal profile, thereby providing the present objective phoropter instrument with added capabilities not generally found on such phoropter instruments.

When performing phoropter measurements, reliance is made on the nominal recorded value of the optical power of the lens or lenses in order to determine the correction power of the lens combination currently presented to the subject. However if there is any error in the true power of the lens or lenses used in the combination currently being used to test the subject's vision, then the correction lens prescribed will be inaccurate. Similarly, if the wheels are not spaced as intended, then the calculation used in combining spaced-apart lenses will be inexact, and again a prescription error will be generated.

Figure 2:
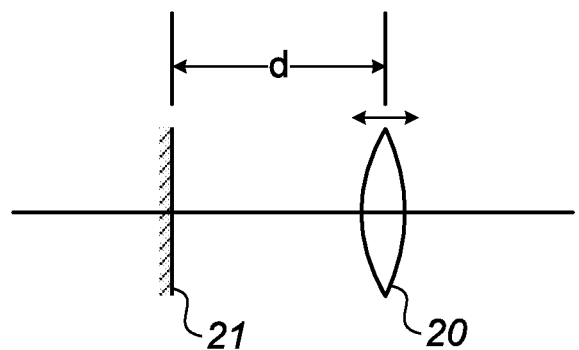
FIG. 2 shows an artificial eye having adjustable aberration levels, which can be used to perform more exact calibration of the lens combinations and wheels used in objective phoropters.

According to the presently described improvement to such a system, a calibration mode is suggested, which can be performed before supply to the customer, on any objective phoropter, such as that described in the above referenced PCT application published as WO/2013/150513. An artificial eye having adjustable aberration levels is used. Such an artificial eye, as shown schematically in FIG. 2, can be simulated by using a lens 20 to simulate the eye lens and a diffusive reflector 21 located at an adjustable distance d behind the lens, to simulate the retina, and to generate the reflection generated therefrom. When the distance d, of the diffusive reflector from the optical center of the lens, is set to be the exact focal length of the lens, the artificial eye replicates a real eye having perfect vision, since any illumination falling on the eye would be accurately focused on the "retina" 21. By moving the diffusive reflector away from the focal plane of the lens, different aberration levels can be generated for the artificial eye, positive or negative spherical powers being determined by the direction of motion of the diffusive reflector. Motion of the diffusive reflector towards the lens will generate an "eye" that requires a correction with positive spherical power, while motion of the diffusive reflector away from the lens will generate an "eye" requiring a correction with negative spherical power. Preliminary calibration tests can be performed to determine the position setting of the diffusive reflector required for any power level required of the artificial eye. Powers of up to +/−20 diopters can be readily obtained.

In order to perform the calibration procedure, an objective phoropter measurement is made on the artificial eye. The artificial eye is first set to have a first preselected level of spherical aberration, and that same level is requested of the instrument, by selecting, according to predetermined algorithms and lookup tables, the correct combination of lenses in the phoropter wheels in order to provide that nominal level of vision correction. The preset aberration of the artificial eye should now be nominally perfectly corrected using the combination of lenses which should supposedly provide perfect correction for that level of aberration of the artificial eye. However, since the lens combination may not have a dioptric value exactly equal to that attributed to the combination selected, either because the power values of one or more of the lenses used in the combination are slightly different from those nominally ascribed thereto, or because of inaccurate spacing of the lens wheels, a residual aberration measurement performed by the wavefront analysis section of the objective phoropter, may not show zero residual aberration. Such a residual aberration can then be attributed to the difference between the nominal dioptric value of the lens combination chosen, and the true optical power of the lens combination used to supposedly "correct" the vision in the artificial eye. The nominal value of that combination can therefore be corrected by subtracting the measured residual power, (taking the sign of the residual optical power into consideration) and the true optical power of that combination recorded in the instrument memory. This procedure can be repeated for each lens combination, such that the true optical power for each combination can be determined by this calibration routine. These true values of optical power can be inserted into the look-up table of the instrument, so that when that lens combination is called on to correct the vision of a subject undergoing the objective phoropter test, its exact value is used rather than a nominal value calculated from the supposed dioptric values ascribed to the combination of the individual lenses. This calibration procedure can be repeated for other combinations of lenses by adjusting the artificial eye to have other aberration levels, and finding the true power of the lens combination selected by the instrument to correct that aberration level of the artificial eye.

Each combination of lenses from all of the lens wheels can thus be measured in this preliminary calibration, resulting in an accurate dioptric value of each of the possible combinations of lenses which the instrument enables. This means that even in complex phoropters having a large number of lens wheels and several lens locations on each wheel (typically up to seven lens wheels with five lenses in each wheel), in which there may be hundreds of combinations of lenses, each combination will have its aberration correction value accurately measured. In the same way that spherical power can be thus calibrated, cylinder can also be accurately calibrated by a preliminary routine using the model eye, and combinations of spherical correction and prism can therefore also be accurately calibrated. The objective phoropter can be programmed to run through this calibration procedure automatically, setting the artificial eye aberration, selecting the appropriate lens combination, making the residual aberration measurement for sequential levels of aberrations, and entering the correct values of each lens combination in the instrument memory, until the complete measurement range has been covered.

Additionally, the data obtained in the pre-calibration routine can enable the instrument to select the lens combination that is known to give the closest correction to that required, even though the nominal value of a different combination, based on the theoretical value of the power of the lenses selected in that different combination, may appear to be closer to that requirement.

Thus, when using the phoropter, each lens combination is accurately determined, and an accurately calibrated measurement can thus be made, resulting in prescriptions for correction lenses having a higher level of accuracy than in prior art instruments. This improved calibration technique becomes important for subjects requiring high values of vision correction, where the lens combination from the different phoropter wheels becomes much more critical than for low power corrections.

The shape and position of the image of the keratometer ring can be used to determine whether the eyes of the subject are accurately centered on the optical axes of the binocular channels, whether the direction of gaze of the subject is correct, and whether the subject's head is correctly aligned straight ahead.

According to one convenient way of using the instrument, in a preliminary step, the eyes of the subject are centered in their respective positions relative to the axes of the measurement channels using the motors incorporated in the machine. The motors are used to center each eye individually and an approximate focus is achieved initially with a manual knob on the forehead rest to move the head backwards and forwards. Further fine tuning is then performed using a motor that moves the complete phoropter housing forwards and backwards along the direction of its optical axes.

The angle of gaze of the subject and the head tilt angle are factors that may affect the alignment process. Gaze angle and horizontal head tilt can be characterized as follows:
(i) Gaze angle: If the patient is not looking in the correct direction, even though his head is aligned correctly forwards, both of the rings will be off-center relative to the optical axis of each eye, and correction is done by asking the patient to look straight at the screen. The operator can discern this situation when both rings are symmetrically aligned.
(ii) Head not straight: The subject has rotated his/her head horizontally about a vertical axis, so that it is not pointing straight forward. The two eyes will have different focus positions relative to the instrument, and the subject must be asked to straighten his/her head, until the focal positions of both eyes are optimized and equal, as per the procedure explained hereinabove.

However, until both of these effects have also been corrected it is not possible to ensure that centering has been achieved with optimum accuracy. Thus if the patient is looking in the correct direction, and his head is also aligned straight ahead, and the keratometric images are not both correctly centered on the screen, that indicates that the subject's eyes are not in their correctly centered positions relative to their respective optical axes, and this situation has to be corrected. Therefore, after ensuring that both the angle of gaze and the head tilt are correct, a final centering correction procedure can be done, by use of the motors incorporated into the instrument, as expounded in the above mentioned International Patent Publication No. WO/2013/150513, using the vertical motors to correct vertical asymmetry, and the pupil distance horizontal motors to correct any horizontal lack of symmetry.

Figure 3:
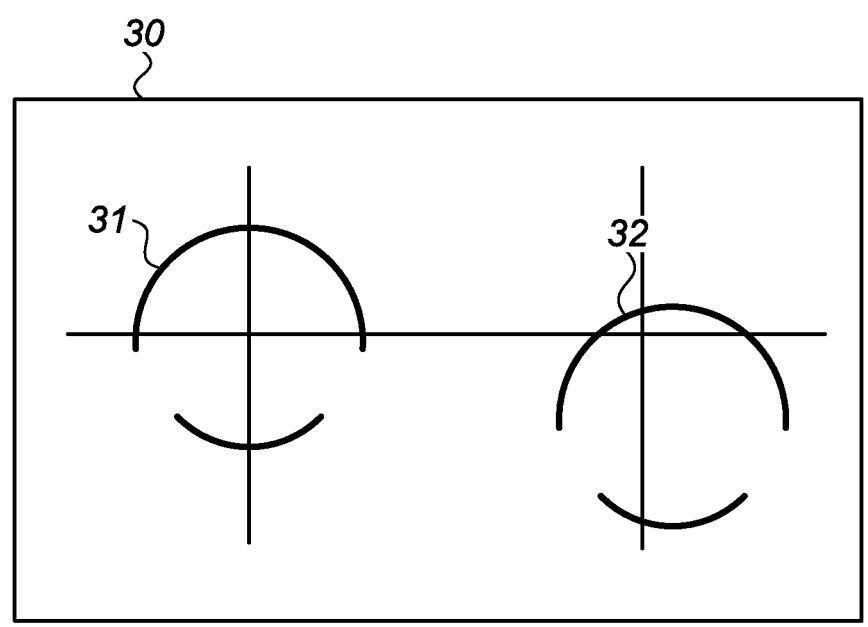
FIG. 3 is a view of the display screen of an improved objective phoropter such as that shown in FIG. 1, showing the manner in which lack of eye centering can be discerned and corrected using the centering methods improvements of the present application.

Reference is made to FIG. 3 which is a view of the display 30 of the instrument during the above described binocular keratometric measurement. The keratometer ring image is shown for both eyes in the binocular vision mode of the instrument. In the example shown in FIG. 3, the keratometer "ring" is not a complete ring, but is divided into two parts. This is done only to enable simpler construction of the instrument. The left-hand eye has a symmetrically positioned image of the ring object 31, indicating that the subject's left eye is properly centered on the axis of the left hand channel. For the right-hand eye however, the ring image 32 is not centered, indicating lack of the correct centering of the instrument relative to the subject's eyes. The centering can be corrected using the horizontal pupil distance (pd) drive, and the vertical motor drives.

The focussing measurements are used for determining incorrect head alignment, since if the subject's head is not aligned such that it is directed straight along the axis of the instrument, the distance of each eye from its correct reference position in the instrument will be different, and this will cause a difference in measured focus position of the two eyes. The subject can then be told to tilt his head in the relevant direction, in order to bring the focus of both eyes to the same and correct positions.

Conventional distant vision objective phoropter measurements are performed using a test chart, which can conveniently be on a display screen, located several meters in front of the subject. In order to perform correct near-vision phoropter measurements, it is necessary for the subject to focus his gaze at a test object located in the near vision field, typically 30 or 40 cm in front of his eyes. According to another implementation of the present instrument, such a test chart is swung into the optical axis at such a distance in front of the subject's eye, and the vision is checked in the near field using the instrument for performing an objective phoropter measurement. The tests screen can also be moved forwards and backwards to adjust the desired near vision distance at which the test is to be performed. The convergence motors can also be used to ensure comfortable alignment of the subject's eyes for the near vision phoropter measurements. Binocular near vision can be tested both subjectively and objectively with this device.

It is appreciated by persons skilled in the art that the present invention is not limited by what has been particularly shown and described hereinabove. Rather the scope of the present invention includes both combinations and sub-combinations of various features described hereinabove as well as variations and modifications thereto which would occur to a person of skill in the art upon reading the above description and which are not in the prior art.

The invention claimed is:

1. An improved accuracy objective phoropter, comprising:
   a combination objective phoropter instrument comprising a wavefront analysis system and a phoropter system incorporating a lens wheel array;
   at least one illuminated object disposed in the field of view of an eye to be measured, and at a predefined distance from said phoropter wheel;
   a camera system positioned such that it captures images of the reflection from the cornea of said eye, of the illumination of said at least one object; and
   a control unit using said images from said camera to generate control instructions to perform at least one of (i) centering an axis of said instrument relative to the center of said eye, and (ii) focusing the position of a lens wheel of said instrument relative to the cornea of said eye.

2. An improved accuracy objective phoropter according to claim 1, further incorporating lateral adjustment mechanisms for said lens wheel array, wherein said control instructions are input to said lateral adjustment mechanisms such that said lens wheel array moves in order to center its axis relative to the center of said eye.

3. An improved accuracy objective phoropter according to claim 1, wherein said center of said eye is determined as the position of the apex of the cornea of said eye.

4. An improved accuracy objective phoropter according to claim 1, wherein said control unit performs said focusing of the position of said lens wheel of said instrument relative to the cornea of said eye, by actuating longitudinal motion mechanisms of said instrument relative to said eye and determining when said images of the reflection from the cornea of said eye of the illumination of said at least one object, have maximum sharpness.

5. An improved accuracy objective phoropter according to claim 1, wherein said at least one illuminated object is at least part of an illuminated ring.

6. An improved accuracy phoropter according to claim 1, wherein said illumination is at a wavelength other than that used for performing said wavefront analysis.

7. An improved accuracy objective phoropter according to claim 1, wherein said control unit is further adapted to determine lack of symmetry of said images of said reflections from the cornea of both of said eyes, said lack of symmetry indicating that the gaze of at least one of said eyes is off-axis.

8. An improved accuracy objective phoropter according to claim 7, wherein said control unit is configured to output control instructions to realign the subject's gaze in order to symmetrize said images of said at least one object.

9. An improved accuracy objective phoropter according to claim 1, wherein said control unit is further adapted to determine lack of simultaneous correct focusing of said images of said reflection of said at least one object from the corneas of both of said eyes, said lack of simultaneous focusing indicating that the head of the subject whose eyes are being measured is not directed straight in the direction of the axis of said objective phoropter.

10. An improved accuracy objective phoropter according to claim 9, wherein said control unit is adapted to output control instructions to realign the subject's head in order to bring the position of both of said eyes to focus simultaneously.

11. An improved accuracy objective phoropter according to claim 10, wherein said control instructions to realign the subject's head comprises instructions for rotation of the subject's head, to bring the head on-axis.

12. An improved accuracy objective phoropter according to claim 1, further comprising a test chart disposed at a distance in front of said eye representative of a near vision test, such that said objective phoropter instrument can determine the near vision correction required by said eye under test.

13. An improved accuracy objective phoropter according to claim 12, wherein said test chart is axially adjustable to different near vision positions.

14. A method of calibrating the phoropter wheel assembly of an objective phoropter incorporating a wavefront analyser, comprising:

positioning in front of a channel of said objective phoropter, an artificial eye having adjustable levels of vision aberration;

selecting a first level of vision aberration of said artificial eye;

selecting a first lens combination from said phoropter wheel assembly having a nominal optical power expected to provide correction to said first selected level of vision aberration of said artificial eye;

using said wavefront analyser to measure the residual level of vision aberration of said artificial eye corrected using said first lens combination;

using said residual level of vision aberration to determine the true optical power of said first lens combination; and repeating said procedure for further selected levels of vision aberration of said artificial eye and corresponding lens combinations from said phoropter wheel assembly.

15. A method according to claim 14 wherein said artificial eye comprises a lens disposed in front of a diffusive reflector.

16. A method according to claim 14 wherein the true optical powers of said lens combinations in said phoropter wheel assembly are stored in a memory of said objective phoropter.

17. A method according to claim 14 wherein said true optical power of said first lens combination is determined by subtracting said measured residual level of vision aberration of said artificial eye from said nominal optical power of said first lens combination corrected using said first lens combination.

* * * * *